(12) United States Patent
Birkmeyer et al.

(10) Patent No.: US 8,828,005 B2
(45) Date of Patent: Sep. 9, 2014

(54) SPINAL FIXATION ELEMENT AND METHODS

(75) Inventors: Paul Birkmeyer, Marshfield, MA (US); Michael Zajack, Marshfield, MA (US); Erasmo Lopez, Seattle, WA (US); Ramon Alberto Ruberte, Ann Arbor, MI (US)

(73) Assignee: DePuy Synthes Products, LLC, Raynham, MA (US)

( * ) Notice: Subject to any disclaimer, the term of this patent is extended or adjusted under 35 U.S.C. 154(b) by 620 days.

(21) Appl. No.: 12/463,578

(22) Filed: May 11, 2009

(65) Prior Publication Data

US 2009/0216328 A1 Aug. 27, 2009

Related U.S. Application Data

(62) Division of application No. 10/708,721, filed on Mar. 19, 2004, now Pat. No. 7,547,318.

(51) Int. Cl.
*A61B 17/70* (2006.01)
*A61B 17/00* (2006.01)

(52) U.S. Cl.
CPC ......... *A61B 17/7037* (2013.01); *A61B 17/7011* (2013.01); *A61B 17/7005* (2013.01); *A61B 17/7032* (2013.01); *A61B 17/7085* (2013.01); *A61B 2017/00238* (2013.01)
USPC ...................................................... 606/86 A

(58) Field of Classification Search
USPC ........... 606/86 A, 96, 99, 246–279, 300–321; 600/201–249
See application file for complete search history.

(56) References Cited

U.S. PATENT DOCUMENTS

| 2,320,709 A | 6/1943 | Arnesen |
| 3,246,646 A | 4/1966 | Murphy |

(Continued)

FOREIGN PATENT DOCUMENTS

| DE | 3434807 | 12/1985 |
| DE | 10027988 | 1/2002 |

(Continued)

OTHER PUBLICATIONS

Kevin T. Foley, M.D., CD Horizon SEXTANT Rod Insertion System and Surgical Technique, pp. 1-30, Meditronic Sofamor Danek, Memphis, TN (Jul. 2002).

(Continued)

*Primary Examiner* — Ellen C Hammond
*Assistant Examiner* — Michelle C Eckman
(74) *Attorney, Agent, or Firm* — Nutter McClennen & Fish LLP

(57) ABSTRACT

A spinal fixation element is provided having a feature formed thereon that facilitates placement of the spinal fixation element through an access device, thus allowing the spinal fixation element to be positioned in relation to a spinal anchor that is coupled to the access device and that is implanted in a vertebra in a patient's spine. The feature also optionally facilitates placement of the spinal fixation element in relation to spinal anchors implanted in adjacent vertebrae. In particular, the spinal fixation element is adapted for use with an access device that has at least one slot or opening formed therein and having a width that is less than a width of the feature, thus preventing the feature from passing therethrough. The spinal fixation element can therefore be inserted through the access device, and a portion of the fixation element can be passed through the slot or opening in the access device while the feature is retained in the access device. As a result, the feature is seated within a spinal anchor that is coupled to the access device, and the remaining portion of the spinal fixation element can extend through the slot, preferably to be positioned within a spinal anchor disposed within an adjacent vertebra.

17 Claims, 11 Drawing Sheets

(56) References Cited

U.S. PATENT DOCUMENTS

| | | | |
|---|---|---|---|
| 3,552,799 A | 1/1971 | Koranda | |
| 4,263,899 A | 4/1981 | Burgin | |
| 4,545,374 A | 10/1985 | Jacobson | |
| 4,686,966 A | 8/1987 | Tsai | |
| 4,765,311 A | 8/1988 | Kulik et al. | |
| 4,872,451 A | 10/1989 | Moore et al. | |
| 4,887,020 A | 12/1989 | Graham | |
| 4,913,134 A | 4/1990 | Luque | |
| 4,961,740 A | 10/1990 | Ray et al. | |
| 5,015,255 A | 5/1991 | Kuslich | |
| 5,024,659 A | 6/1991 | Sjostrom | |
| 5,052,372 A | 10/1991 | Shapiro | |
| 5,084,053 A | 1/1992 | Ender | |
| 5,171,279 A | 12/1992 | Mathews | |
| 5,231,973 A | 8/1993 | Dickie | |
| 5,242,443 A | 9/1993 | Kambin | |
| 5,242,446 A | 9/1993 | Steffee et al. | |
| 5,324,290 A | 6/1994 | Zdeblick et al. | |
| 5,360,431 A * | 11/1994 | Puno et al. | 606/308 |
| 5,395,317 A | 3/1995 | Kambin | |
| 5,484,440 A * | 1/1996 | Allard | 606/916 |
| 5,520,610 A | 5/1996 | Giglio et al. | |
| 5,540,688 A * | 7/1996 | Navas | 606/266 |
| 5,569,248 A | 10/1996 | Mathews | |
| 5,647,873 A | 7/1997 | Errico et al. | |
| 5,728,097 A | 3/1998 | Mathews | |
| 5,749,884 A | 5/1998 | Benderev et al. | |
| 5,766,221 A | 6/1998 | Benderev et al. | |
| 5,817,094 A | 10/1998 | Errico et al. | |
| 5,928,139 A | 7/1999 | Koros et al. | |
| 5,931,777 A | 8/1999 | Sava | |
| 5,954,635 A | 9/1999 | Foley et al. | |
| 5,984,923 A * | 11/1999 | Breard | 606/259 |
| 6,004,326 A | 12/1999 | Castro et al. | |
| 6,033,406 A | 3/2000 | Mathews | |
| 6,053,921 A | 4/2000 | Wagner et al. | |
| 6,139,493 A | 10/2000 | Koros et al. | |
| 6,159,179 A | 12/2000 | Simonson | |
| 6,183,472 B1 * | 2/2001 | Lutz | 606/86 A |
| 6,200,322 B1 | 3/2001 | Branch et al. | |
| 6,224,545 B1 | 5/2001 | Cocchia et al. | |
| 6,224,548 B1 | 5/2001 | Gopinathan et al. | |
| 6,226,548 B1 | 5/2001 | Foley et al. | |
| 6,235,028 B1 | 5/2001 | Brumfield et al. | |
| 6,250,322 B1 | 6/2001 | Porter | |
| 6,267,765 B1 * | 7/2001 | Taylor et al. | 606/86 A |
| 6,299,616 B1 | 10/2001 | Beger | |
| 6,331,179 B1 | 12/2001 | Freid et al. | |
| 6,485,491 B1 | 11/2002 | Farris et al. | |
| 6,520,907 B1 | 2/2003 | Foley et al. | |
| 6,530,926 B1 | 3/2003 | Davison | |
| 6,530,929 B1 | 3/2003 | Justis et al. | |
| 6,540,749 B2 | 4/2003 | Schafer et al. | |
| 6,554,831 B1 | 4/2003 | Rivard et al. | |
| 6,607,530 B1 | 8/2003 | Carl et al. | |
| 6,652,527 B2 | 11/2003 | Zucherman et al. | |
| 6,682,529 B2 | 1/2004 | Stahurski | |
| 6,740,086 B2 | 5/2004 | Richelsoph | |
| 6,740,089 B2 | 5/2004 | Haider | |
| 6,743,231 B1 | 6/2004 | Gray et al. | |
| 6,793,656 B1 | 9/2004 | Mathews | |
| 6,802,844 B2 | 10/2004 | Ferree | |
| 6,849,064 B2 | 2/2005 | Hamada | |
| 6,929,647 B2 | 8/2005 | Cohen | |
| 7,179,225 B2 | 2/2007 | Shluzas et al. | |
| 7,306,603 B2 | 12/2007 | Boehm, Jr. et al. | |
| 7,547,318 B2 | 6/2009 | Birkmeyer et al. | |
| 2001/0001119 A1 | 5/2001 | Lombardo | |
| 2002/0011600 A1 | 1/2002 | Kurahashi et al. | |
| 2002/0049368 A1 | 4/2002 | Ritland | |
| 2002/0068975 A1 | 6/2002 | Teitelbaum et al. | |
| 2002/0082600 A1 | 6/2002 | Shaolian et al. | |
| 2002/0116000 A1 | 8/2002 | Zucherman et al. | |
| 2002/0116006 A1 | 8/2002 | Cohen | |
| 2002/0123668 A1 | 9/2002 | Ritland | |
| 2002/0138077 A1 | 9/2002 | Ferree | |
| 2002/0161368 A1 | 10/2002 | Foley et al. | |
| 2002/0169448 A1 | 11/2002 | Vanacker | |
| 2002/0198526 A1 | 12/2002 | Shaolian et al. | |
| 2003/0060826 A1 | 3/2003 | Foley et al. | |
| 2003/0083657 A1 | 5/2003 | Drewry et al. | |
| 2003/0083688 A1 | 5/2003 | Simonson | |
| 2003/0083689 A1 | 5/2003 | Simonson | |
| 2003/0130659 A1 | 7/2003 | Haider | |
| 2003/0191371 A1 | 10/2003 | Smith et al. | |
| 2003/0194371 A1 | 10/2003 | Lehmann et al. | |
| 2003/0195549 A1 | 10/2003 | Davison et al. | |
| 2003/0195550 A1 | 10/2003 | Davison et al. | |
| 2003/0195551 A1 | 10/2003 | Davison et al. | |
| 2003/0199885 A1 | 10/2003 | Davison et al. | |
| 2003/0208203 A1 | 11/2003 | Lim et al. | |
| 2003/0229347 A1 | 12/2003 | Sherman et al. | |
| 2004/0039384 A1 * | 2/2004 | Boehm et al. | 606/61 |
| 2004/0082961 A1 | 4/2004 | Teitelbaum | |
| 2004/0138662 A1 * | 7/2004 | Landry et al. | 606/61 |
| 2004/0143265 A1 * | 7/2004 | Landry et al. | 606/61 |
| 2004/0162560 A1 | 8/2004 | Raynor et al. | |
| 2004/0172022 A1 | 9/2004 | Landry et al. | |
| 2004/0267277 A1 | 12/2004 | Zannis et al. | |
| 2005/0013407 A1 | 1/2005 | Scheuering | |
| 2005/0038434 A1 | 2/2005 | Mathews | |
| 2005/0065517 A1 | 3/2005 | Chin | |
| 2005/0085813 A1 * | 4/2005 | Spitler et al. | 606/61 |
| 2005/0131406 A1 | 6/2005 | Reiley et al. | |
| 2005/0131407 A1 | 6/2005 | Sicvol et al. | |
| 2005/0131408 A1 * | 6/2005 | Sicvol et al. | 606/61 |
| 2005/0131420 A1 * | 6/2005 | Techiera et al. | 606/99 |
| 2005/0131421 A1 * | 6/2005 | Anderson et al. | 606/99 |
| 2005/0131422 A1 * | 6/2005 | Anderson et al. | 606/104 |
| 2005/0171540 A1 | 8/2005 | Lim et al. | |
| 2005/0182410 A1 | 8/2005 | Jackson | |
| 2005/0192570 A1 | 9/2005 | Jackson | |
| 2005/0192579 A1 * | 9/2005 | Jackson | 606/72 |
| 2005/0192589 A1 * | 9/2005 | Raymond et al. | 606/99 |
| 2006/0217719 A1 * | 9/2006 | Albert et al. | 606/61 |
| 2008/0082103 A1 * | 4/2008 | Hutton et al. | 606/73 |
| 2008/0183214 A1 * | 7/2008 | Copp et al. | 606/265 |

FOREIGN PATENT DOCUMENTS

| | | |
|---|---|---|
| DE | 29810798 | 5/2004 |
| EP | 0528562 | 2/1993 |
| EP | 1190678 | 3/2002 |
| FR | 2729291 | 7/1996 |
| FR | 2796545 | 1/2001 |
| WO | 9205742 | 4/1992 |
| WO | 9308745 | 5/1993 |
| WO | 02076315 | 10/2002 |
| WO | 2004/004100 | 1/2004 |
| WO | 2005/041799 | 5/2005 |

OTHER PUBLICATIONS

Stephen L. Ritland, M.D., Surgical Technique: Micro-TLIF "A Mini-Open and Intermuscular Transforaminal Lumber Interbody Fusion," Aperture Spinal Access System, pp. 1-20, DePuy AcroMed, Inc., Raynham, MA (Oct. 2002).

The Dilation Retractor System, Bright Medical Instruments, Boca Raton, FL.

Speer, et al., "An Arthroscopic Technique for Anterior Stabiliatin of the Shoulder with a Bioabsorbable Tack," J. Bone Joint Surg Am. 1996; 78:1801-7.

Muller, et al., "A Keyhole Approach for Endoscopically Assisted Pedicle Screw Fixation in Lumbar Spine Instability," Neurosurgery, vol. 47, No. 1, Jul. 2000.

* cited by examiner

SPINAL FIXATION ELEMENT AND METHODS

CROSS REFERENCE TO RELATED APPLICATIONS

The present application is a divisional of U.S. application Ser. No. 10/708,721 filed on Mar. 19, 2004 and entitled "Spinal Fixation Element and Methods," which is hereby incorporated by reference in its entirety.

FIELD OF THE INVENTION

This application relates to methods and devices for use in spinal surgery, and in particular to a spinal fixation element, tools, and methods for use in minimally invasive spinal surgery.

BACKGROUND OF THE INVENTION

Spinal fusion is a procedure that involves joining two or more adjacent vertebrae with a bone fixation device so that they no longer are able to move relative to each other. For a number of known reasons, spinal fusion devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Recently, the trend in spinal surgery has been moving toward providing minimally invasive devices and methods for implanting spinal fixation devices. However, generally elongate spinal fixation elements can be difficult to implant using minimally invasive techniques. One such method, for example, utilizes two access devices for introducing an anchoring device, such as a spinal screw, into adjacent vertebrae. A spinal rod is then introduced through a third incision a distance apart from the access sites, and the rod is transversely moved through tissue and muscle into the rod-engaging portion of each spinal screw. The access devices can then be used to apply closure mechanisms to the rod-engaging heads to lock the rod therein. While this procedure offers advantages over prior art invasive techniques, the transverse introduction of the rod can cause significant damage to surrounding tissue and muscle. Moreover, the use of three separate access sites can undesirably lengthen the surgical procedure.

Accordingly, there remains a need for improved minimally invasive devices and methods for introducing a spinal fixation element into a patient's spine.

SUMMARY OF THE INVENTION

The present invention generally provides a spinal fixation element, such as a spinal rod, having a feature formed thereon, preferably at or adjacent to a terminal end thereof. The feature can be, for example, a spherical or bulbous protrusion that extends radially outward from the spinal fixation element. In use, the feature allows the spinal fixation element to be captured by an access device to facilitate placement of the spinal fixation element in relation to a spinal anchor coupled to the access device and implanted in a vertebra in a patient's spine, and optionally to facilitate placement of the spinal fixation element in relation to spinal anchors implanted in adjacent vertebrae.

In one embodiment, the spinal fixation element can be provided as part of a spinal implant kit containing an access device having an inner lumen extending between proximal and distal ends, and at least one opening formed in a sidewall thereof adjacent to the distal end. The sidewall opening(s) in the access device can vary in shape and size, but it preferably extends from the distal end of the access device and terminates distal to the proximal end of the access device, and more preferably the opening(s) has a length that is greater than a length of the spinal fixation element. In an exemplary embodiment, the access device includes opposed openings formed therein. In use, the feature on the spinal fixation element can be sized to prevent passage thereof through the opening, and more preferably the feature has a width that is greater than a width of the opening in the sidewall of the access device to prevent passage of the feature therethrough, thus facilitating positioning of the spinal fixation element with respect to a spinal anchor coupled to the access device.

The spinal implant kit can also optionally include a pusher member that is adapted to advance the spinal fixation element in a distal direction within the access device. In an exemplary embodiment, the pusher member is slidably disposable within the opening in the sidewall of the access device such that it is effective to cause at least a portion of the spinal fixation element to extend through the opening in the sidewall. An actuating member, such as a handle or lever, can be provided for moving the pusher member between a first, proximal position and a second, distal position.

The present invention also provides a method for implanting a spinal fixation element into at least one spinal anchor disposed within a vertebra in a patient's spinal column. In general, the method includes the step of introducing a spinal fixation element having a feature formed thereon adjacent to a terminal end thereof through a lumen in an access device coupled to a spinal anchor. The access device has a slot formed in a sidewall adjacent to a distal end thereof that is adapted to prevent the feature from passing therethrough. The spinal fixation element is then manipulated using, for example, a pusher member, to cause the feature to sit within a receiving member of the spinal anchor coupled to the access device, and to cause a remaining portion of the spinal fixation element to extend through the slot. The remaining portion of the spinal fixation element is preferably positioned within a receiving member of a spinal anchor disposed within an adjacent vertebra in a patient's spinal column. The feature can then be locked with respect to the spinal anchor to fixedly secure the spinal fixation element to the spinal anchor.

In another embodiment of the present invention, a method for implanting a spinal fixation element is provided using at least two spinal anchors implanted in adjacent vertebrae of a patient's spine, and an access device having an inner lumen extending between proximal and distal ends. The distal end of the access device is adapted to couple to one of the spinal anchors, and a slot is formed in a sidewall of the access device adjacent to the distal end. The method includes the steps of providing a spinal fixation element having a first end and a second end with a feature formed thereon and having a width that is greater than a width of the slot in the sidewall of the access device, inserting the spinal fixation element through the lumen in the access device, and manipulating the spinal fixation element to cause the feature to be positioned within the spinal anchor attached to the access device and the first end to extend through the slot such that the spinal fixation element extends between the spinal anchors implanted in adjacent vertebrae.

DETAILED DESCRIPTION OF THE INVENTION

The present invention provides a spinal fixation element, such as a spinal rod, having a feature formed thereon that facilitates placement of the spinal fixation element through an access device, thus allowing the spinal fixation element to be positioned in relation to a spinal anchor that is coupled to the access device and that is implanted in a vertebra in a patient's spine. The feature also optionally facilitates placement of the spinal fixation element in relation to one or more spinal anchors implanted in adjacent vertebrae. In particular, the spinal fixation element is adapted for use with an access device that has at least one slot or opening formed therein and having a width that is less than a width of the feature, thus preventing the feature from passing therethrough. The spinal fixation element can therefore be inserted through the access device, and a portion of the fixation element can be passed through the slot or opening in the access device while the feature is retained in the access device. As a result, the feature is seated within a spinal anchor that is coupled to the access device, and the remaining portion of the spinal fixation element can be positioned within a spinal anchor implanted in an adjacent vertebra.

Figure 1A:
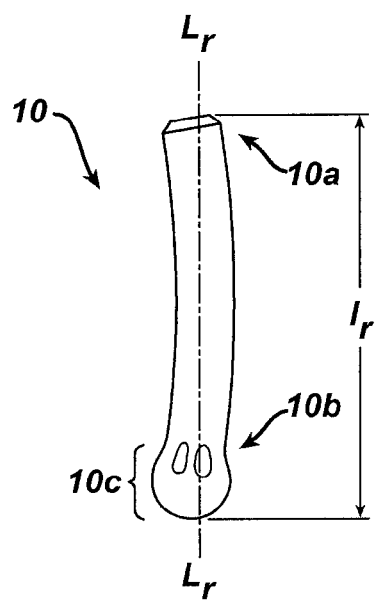
FIG. 1A is a perspective view of one embodiment of a spinal fixation element having a feature formed thereon in accordance with the present invention.

FIG. 1A illustrates an exemplary embodiment of a spinal fixation element 10 in accordance with the present invention. As shown, the spinal fixation element 10 is in the form of an elongate spinal rod having opposed first and second terminal ends 10a, 10b. The fixation element 10 can have any shape and size, and it can be substantially straight or it can have a curved profile, as shown, depending on the intended use. The fixation element 10 also includes a feature that is preferably formed on or adjacent to a terminal end 10a, 10b of the fixation element 10. While the feature can have any shape, FIG. 1A illustrates an exemplary embodiment of a feature 10c formed on the second end 10b of the fixation element 10 and having a generally spherical or bulbous shape. While not shown, the feature 10c can optionally include a flattened portion that extends in a direction that is substantially perpendicular to a generally longitudinal axis $L_r$ of the spinal fixation element 10. The use of a flattened portion is particularly advantageous in that it allows a closure mechanism to be applied to the receiver head of a spinal anchor containing the feature 10c of the spinal fixation element 10, as will be discussed in more detail below. The size of the feature 10c can also vary, but it should have a size that allows the feature 10c to be captured within an access device, and that allows it to be disposed within a receiver head of a spinal anchor, which will also be discussed in more detail below.

Figure 1B:
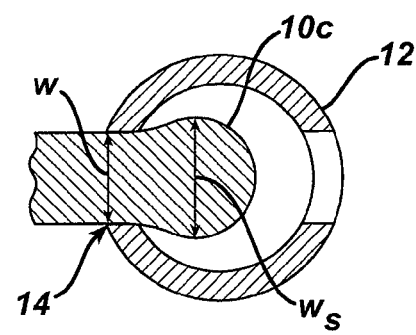
FIG. 1B is a cross-sectional view of a portion of the spinal fixation element of FIG. 1A extending through an opening formed in a sidewall of an access device such that the feature is captured within an inner lumen of the access device.
Figure 1C:
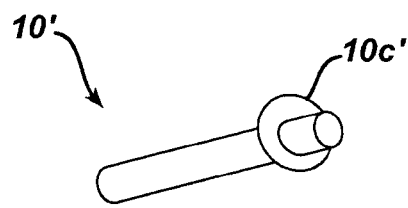
FIG. 1C is a perspective view of another embodiment of a spinal fixation element having a feature formed thereon in accordance with the present invention.

A person skilled in the art will appreciate that the feature 10c formed on the spinal fixation element 10 can have a variety of other configurations, and it can be formed anywhere on the spinal fixation element 10. By way of non-limiting example, the feature 10c can be substantially square or rectangular, or it can have some other shape that protrudes outward from the spinal fixation element. By way of non-limiting example, FIG. 1C illustrates a spinal fixation element 10' having an annular protrusion 10c' formed therein. Regardless of the shape and size of the feature, the shape and size should be adapted to be captured by an access device used in connection with the spinal fixation element.

Figure 2A:
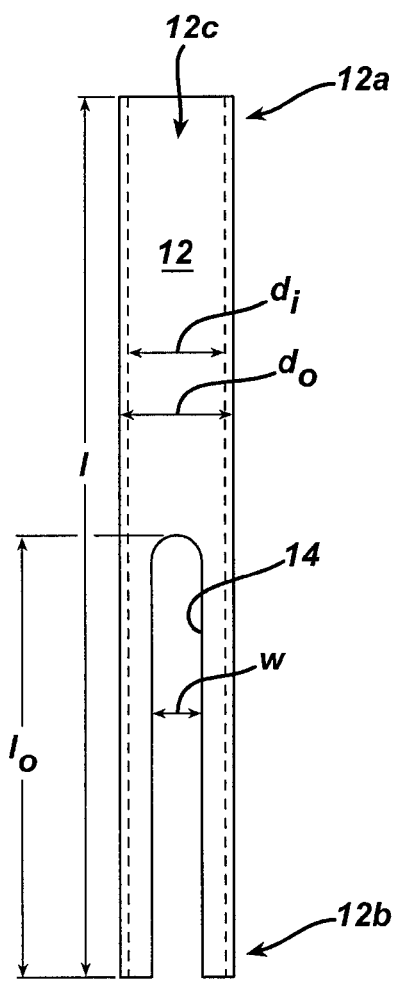
FIG. 2A is a side view of one embodiment of an access device for use with a spinal fixation element in accordance with the present invention.

Virtually any access device can be used with a spinal fixation element in accordance with the present invention, and the configuration of the access device can vary depending on the configuration of the spinal fixation element, and in particular of the feature formed on the spinal fixation element. By way of non-limiting example, FIG. 2A illustrates an exemplary embodiment of an access device 12 for use in connection with the spinal fixation element 10 shown in FIG. 1A. As shown, the access device 12 is in the form of a generally elongate, cylindrical tube having an inner lumen 12c formed therein and defining a longitudinal axis L that extends between proximal and distal ends 12a, 12b thereof. The size of the access device 12 can vary depending on the intended use, but it should have a length l that allows the proximal end 12a of the access device 12 to be positioned outside the patient's body, while the distal end 12b of the access device 12 is coupled to, or positioned adjacent to, a spinal anchor that is implanted in a vertebra in a patient's spine. The access device 12 is also preferably a percutaneous access device 12 such that it is adapted to provide a minimally invasive pathway for the delivery of a spinal fixation element therethrough. In particular, the percutaneous access device 12 preferably has an outer diameter $d_o$ that allows the access device 12 to be implanted through a minimally invasive percutaneous incision, which is a relatively small incision that typically has a length that is less than a diameter or width of the device being inserted therethrough. The inner diameter $d_i$ of the device 12 can also vary, but it should be sufficient to allow the spinal fixation element 10 to be introduced therethrough, preferably in a lengthwise orientation. As will be discussed in more detail below, the inner diameter $d_i$ can also be configured to allow a pusher member to be introduced therethrough for manipulating the spinal fixation element, and it can also be configured to allow a driver mechanism to be introduced therethrough for applying a closure mechanism to lock the spinal fixation element in relation to a spinal anchor.

As is further shown in FIG. 2A, the access device 12 includes at least one sidewall opening or slot 14 formed therein, and more preferably it includes two opposed sidewall openings (only one opening 14 is shown) formed therein and extending proximally from the distal end 12b thereof. One or both openings can be configured for use with spinal fixation element 10, however only opening 14 is described herein. The shape and size of the opening 14 can vary depending on the shape and size of the feature 10c on the spinal fixation element 10, but the opening 14 should be effective to capture the feature 10c within the access device 12. More particularly, the opening 14 should have a width w that is less than a width $w_f$ of the feature 10c on the spinal fixation element 10 to prevent passage of the feature 10c therethrough, as shown in FIG. 1B. The opening 14 can also extend over about half of the length l, or less than half of the length l, of the access device 12, but more preferably the opening 14 has a length $l_o$ that is greater than a length $l_r$ (FIG. 1A) of the spinal fixation element 10. In use, the spinal fixation element 10 can be introduced through the device 12 in a first, lengthwise orientation, in which the spinal fixation element 10 is substantially parallel to the longitudinal axis L (FIG. 2B) of the access device 12. The feature 10c will be retained within the access device 12, and the remainder of the spinal fixation element 10 can be manipulated to extend through the slot 14 in the access device 12 to position it in a second orientation at an angle with respect to the first orientation. Since the length L of the spinal fixation element 10 will necessarily be greater than the inner diameter $d_i$ of the access device 12, the opening 14 allows the spinal fixation element 10 to pass therethrough while being transitioned from the first, lengthwise orientation to the second orientation. By capturing the feature 10c within the access device 12, placement of the remainder of the spinal fixation element 10 within a spinal anchor implanted in an adjacent vertebra can be facilitated.

A person skilled in the art will appreciate that the access device 12 can include any number of sidewall openings having any shape and size that is sufficient to allow a spinal fixation element in accordance with the present invention to be moved from the first orientation to the second orientation while preventing passage of the feature therethrough.

Figure 2B:
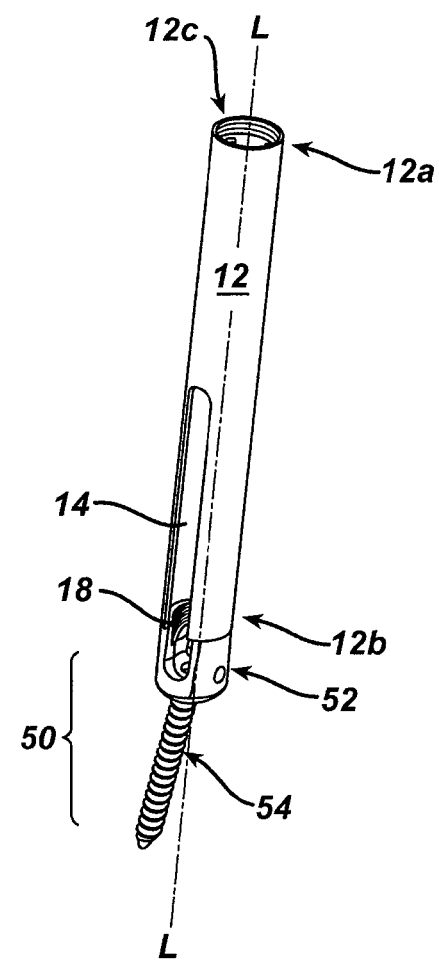
FIG. 2B is a perspective view of the access device shown in FIG. 2A mated to one embodiment of a spinal anchor in accordance with the present invention.

As indicated above, the access device 12 is adapted to couple to a spinal anchor 50, as shown in FIG. 2B, to facilitate placement of the spinal fixation element 10 with respect to one or more spinal anchors implanted in adjacent vertebrae in a patient's spinal column. Accordingly, the distal end 12c of the access device 12 can include one or more mating elements 18 formed thereon or therein for engaging the anchor 50. Suitable mating elements include, for example, threads, a twist-lock engagement, a snap-on engagement, or any other technique known in the art, and in an exemplary embodiment the mating elements are formed on an inner surface of the distal end 12b of the access device 12. Exemplary techniques for mating the access device 12 to an anchor are disclosed in U.S. patent application Ser. No. 10/738,286, entitled "Percutaneous Access Devices and Bone Anchor Assemblies," filed on Dec. 16, 2003. A person skilled in the art will appreciate that a variety of other techniques can be used to removably mate the access device to an anchor.

FIG. 2B further illustrates an exemplary spinal anchor, e.g., spinal screw 50, for use with the methods and devices of the present invention. While screw 50 is shown, a variety of other anchors can be used with the devices and methods of the present invention including, for example, spinal hooks, bolts, wires/cables, etc. As shown in FIG. 2B, the spinal screw 50 includes a distal, bone-engaging portion, e.g., a threaded shank 54, and a proximal, U-shaped, receiver head 52 that is adapted to seat the spinal fixation element 10, and more particularly that is adapted to seat the feature 10c formed on the spinal fixation element 10. The threaded shank 54 can be fixedly attached to the receiver head 52 to form a monoaxial screw, or alternatively the shank 54 can be configured as a polyaxial screw, as shown, that is rotatably disposed through an opening formed in the distal end of the receiver head 52 to allow rotation of the shank 54 with respect to the receiver head 52. A variety of techniques can be used to allow rotation of the head 52 with respect to the shank 54.

The present invention also provides methods for implanting a spinal fixation element within one of more spinal anchors implanted in one or more adjacent vertebrae in a patient's spinal column. An exemplary method for implanting the spinal anchors and for attaching an access device to at least one of the anchors is described in more detail in U.S. patent application Ser. No. 10/738,130, entitled "Methods and Devices for Minimally Invasive Spinal Fixation Element Placement," filed on Dec. 16, 2003. A person skilled in the art will appreciate that, while the method is shown and described in connection with access device 12 and spinal screw 50 disclosed herein, the method is not limited to use with such devices, and a variety of other devices known in the art can be used. Moreover, while two access devices 12, 12' and two anchors 50, 50' are shown, the method of the present invention can be performed using any number of access devices and anchors. The method can also be performed using only some of the method steps disclosed herein, and/or using other methods known in the art.

Figure 3A:
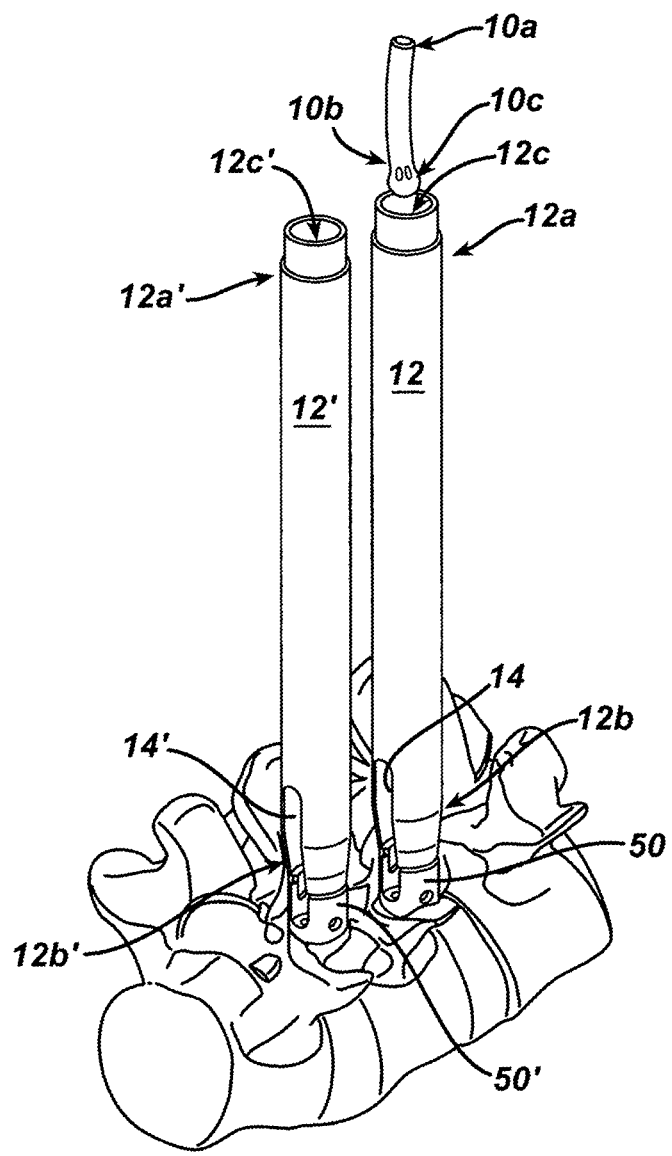
FIG. 3A is a perspective view illustration of first and second access devices coupled to first and second spinal anchors implanted in adjacent vertebrae in a patient's spinal column, showing the spinal fixation element of FIG. 1A being introduced through a proximal end of the first access device with the feature leading.
Figure 3B:
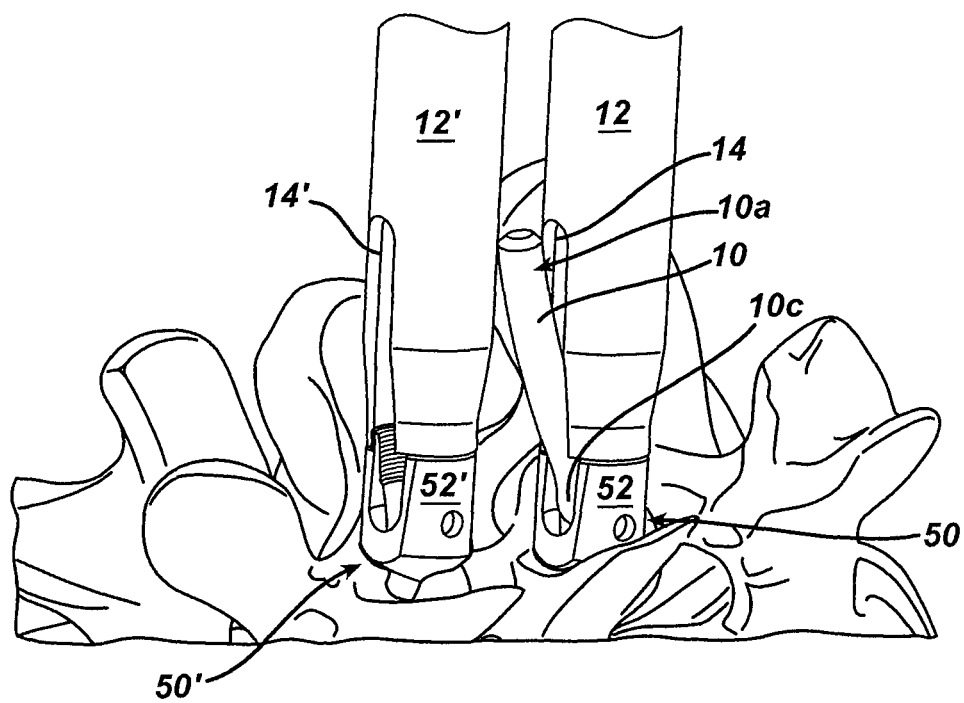
FIG. 3B is a perspective view illustration of the spinal fixation element shown in FIG. 3A being manipulated to extend through the opening of the first access device.
Figure 3C:
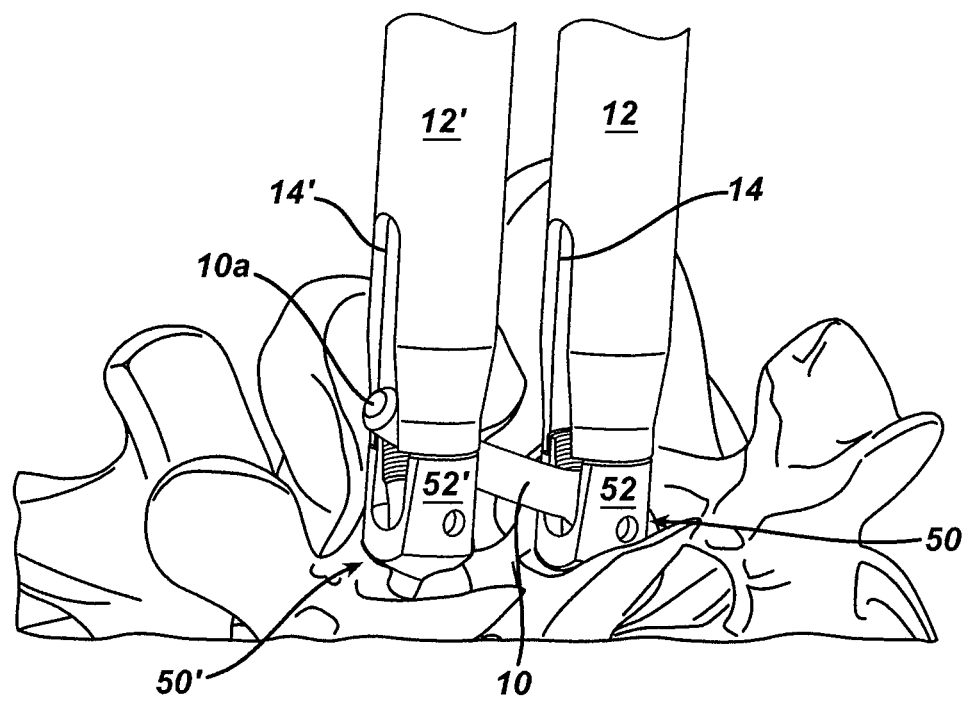
FIG. 3C is a perspective view illustration of the spinal fixation element shown in FIG. 3B being further manipulated to be positioned within the spinal anchor attached to the second access device and disposed within an adjacent vertebra.

FIG. 3A-3C illustrate one method for implanting a spinal fixation element having a feature formed thereon through an access device. As shown in FIG. 3A, the spinal fixation element 10 is inserted into the lumen 12c in the proximal end 12a of the access device 12 in a lengthwise orientation with the feature 10c leading, and the opposed terminal end, e.g., the first end 10a, of the spinal fixation element 10 trailing. The spinal fixation element 10 is then advanced toward the distal end 12b of the access device 12 until the feature 10c is positioned within the receiver head 52 of the spinal anchor 50, as shown in FIG. 3B. The remainder of the fixation element 10 can then be manipulated to move it from the first, lengthwise orientation to a second orientation, in which the spinal fixation element 10 extends through the slot 14 formed in the access device 12. Since the feature has a width $w_f$ that is greater than a width w of the slot 14, the feature is retained within the access device 12, as is further shown in FIG. 3B. As a result, the remainder of the fixation element 10 can be positioned within a receiver head 52' of the spinal anchor 50' disposed within an adjacent vertebra, as shown in FIG. 3C. The spinal fixation element 10 can then be locked to each spinal anchor 50, 50', preferably by applying a closure mechanism (not shown) to the receiver head 52, 52' of each anchor 50, 50'. Virtually any closure mechanism can be used to lock the spinal fixation element 10 within each receiver head 52, 52' including, for example, a threaded or twist-lock closure cap. Where the feature 10c on the fixation element 10 includes a flattened surface (not shown), the flattened surface should be positioned such that is faces the proximal end 12a of the access device 12, thus allowing the closure cap to rest against the flattened surface when it is applied to the receiver head 52 on the anchor 50.

The present invention also provides a pusher member that can optionally be used to facilitate movement of the fixation element 10 from the first to the second orientation. The pusher member can be an elongate member for advancing the spinal fixation element 10 in a distal direction, and/or it can include an engagement mechanism to engage and manipulate the spinal fixation element 10. By way of non-limiting example, U.S. patent application Ser. No. 10/737,538, entitled "Pivoting Implant Holder," filed on Dec. 16, 2003, discloses various pusher members that can be used with the present invention.

Figure 4A:
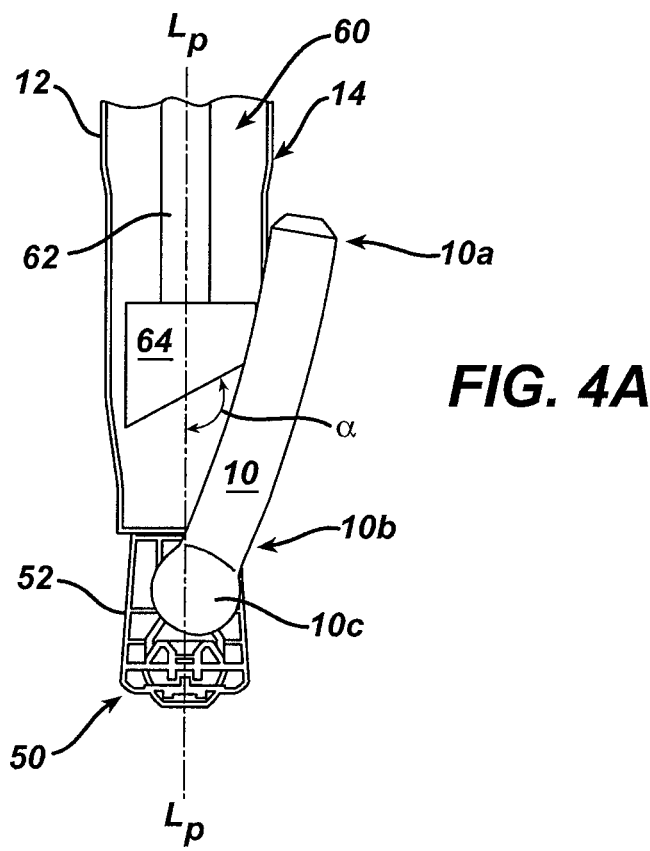
FIG. 4A is a cross-sectional view illustration of one embodiment of a pusher member in accordance with the present invention, showing the pusher member being used to manipulate a spinal fixation element to cause the feature on the spinal fixation element to sit within a spinal anchor attached to the access device, and to cause the remaining portion of the spinal fixation element to extend through the opening in an access device.
Figure 4B:
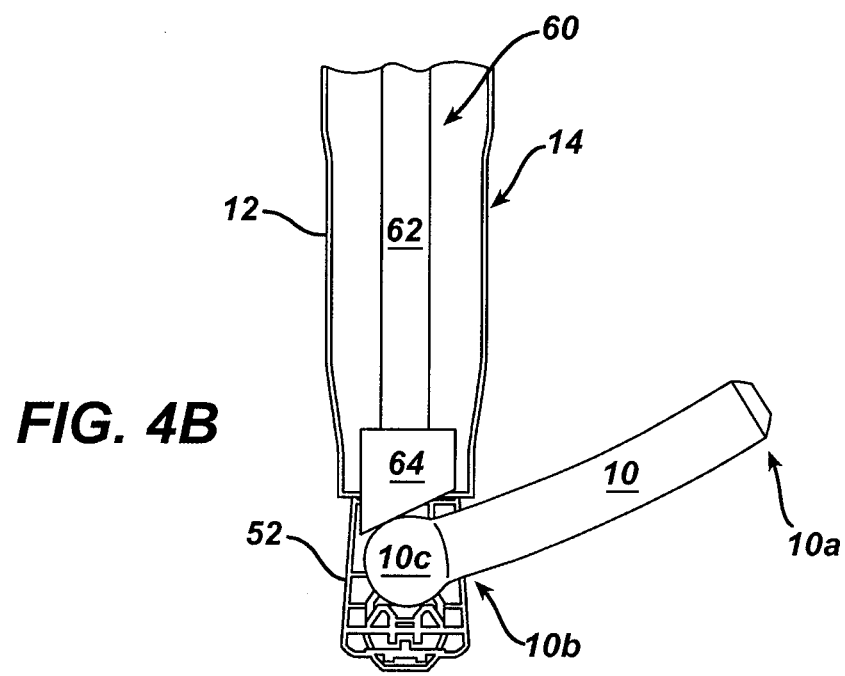
FIG. 4B is a cross-sectional view illustration of the spinal fixation element shown in FIG. 4A being further manipulated to extend through the opening in the access device.

FIGS. 4A and 4B illustrate one exemplary embodiment of a pusher member 60 for use with the present invention. As shown, the pusher member 60 is in the form of an elongate shaft 62 having a distal pusher portion 64 that is configured to be slidably disposed within the lumen 12c in the access device 12. The distal pusher portion 64 has a substantially wedge-like shape such that a distal-most surface 65 of the distal pusher portion 64 is disposed at an angle α with respect to a longitudinal axis $L_p$ of the pusher member 60. This allows the pusher member 60 to direct the spinal fixation element 10 through the slot 14 in the access device 12, as shown in FIGS. 4A and 4B, thereby facilitating positioning of the spinal fixation element 10, preferably with respect to one or more spinal anchors implanted in adjacent vertebrae.

Figure 5A:
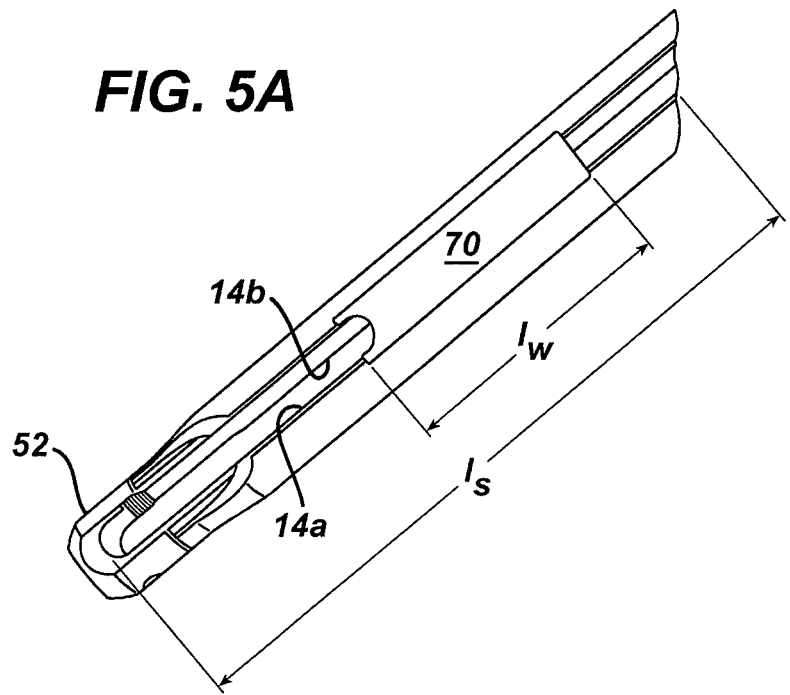
FIG. 5A is a side perspective view illustration of another embodiment of a pusher member in accordance with the present invention.
Figure 5B:
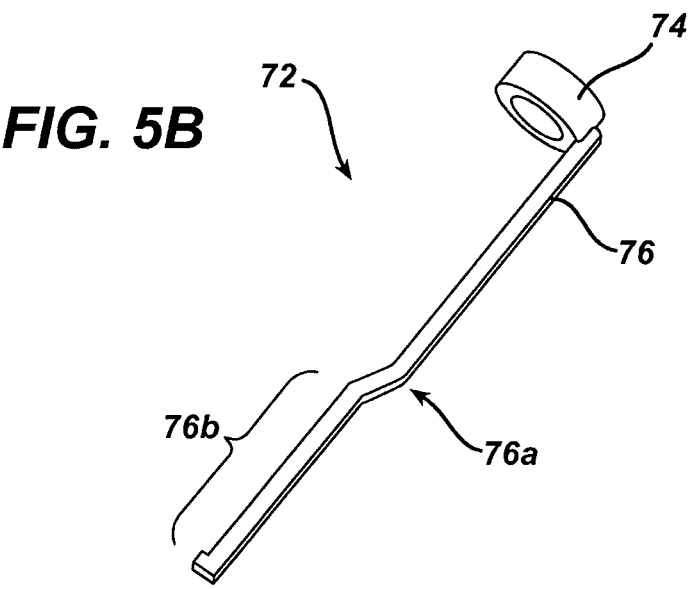
FIG. 5B is a side perspective view illustration of an actuating member for use with the pusher member shown in FIG. 5A.
Figure 5C:
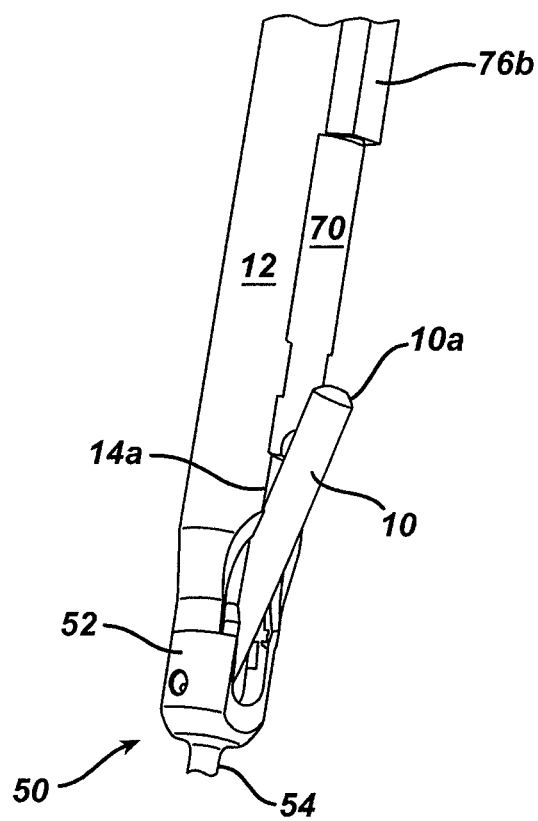
FIG. 5C is a side perspective view illustration of the pusher member of FIG. 5A and the actuating member of FIG. 5B, showing the actuating member being used to advance the pusher member from a proximal position to a distal position such that it is effective to cause a portion of a spinal fixation element to extend through the opening in the access device.

FIGS. 5A-5C illustrate another embodiment of a pusher member for manipulating the spinal fixation element 10 to cause it to extend through the slot 14 formed in the access device 12. In this embodiment, the pusher member is in the form of a pusher window 70 that is slidably disposed within a slot formed in the access device 12. FIG. 5A illustrates two slots 14a, 14b formed in the access device 12, and the pusher window 70 is shown disposed within slot 14a. The pusher window 70 preferably only extends across a portion of the slot 14a, and in particular it preferably has a length $l_w$ that is less than a length $l_s$ of the slot 14a, only a portion of which is shown in FIG. 5A. In use, the pusher window 70 is movable along the longitudinal axis L of the device 12 between the first, proximal position, and a second, distal position. An actuating mechanism, such as a lever that is coupled to the sliding window 70, can be provided for controlling movement of the sliding window 70 between the first and second positions. While virtually any actuating member can be used, FIG. 5B illustrates an actuating member 72 having a proximal o-ring portion 74 that is adapted to be slidably disposed around the access device 12, and an elongate member 76 that extends distally from the proximal o-ring portion 74. The elongate member 76 includes at least one bend 76a formed therein that allows a distal portion 76b of the elongate member 76 to extend into and be positioned within the slot 14a formed in the access device 12. In use, the o-ring 76 on the actuating member 72 is positioned around the access device 12 such that the distal portion 76b is seated within the slot 14a formed in the access device 12 at a position that is proximal to the position of the pusher window 70, as shown in FIG. 5C. The actuating member 72 can then be moved distally, thereby causing the pusher window 70 to move in a distal direction. When the spinal fixation element 10 is disposed within the access device 12, a trailing end, e.g., first end 10a, will at least partially be positioned within the slot 14a. Thus, distal movement of the pusher window 70 will be effective to further guide the fixation device 10 through the slot 14a, preferably toward a spinal anchor that is implanted in an adjacent vertebra. The pusher window 70 is particularly useful with spinal fixation elements 10 that have a curved configuration, as the curvature of the spinal fixation element 10 will cause a portion of the fixation element 10 to extend into the slot 14, thus allowing the pusher window 70 to engage the fixation element 10 and force it into the second orientation.

Figure 6A:
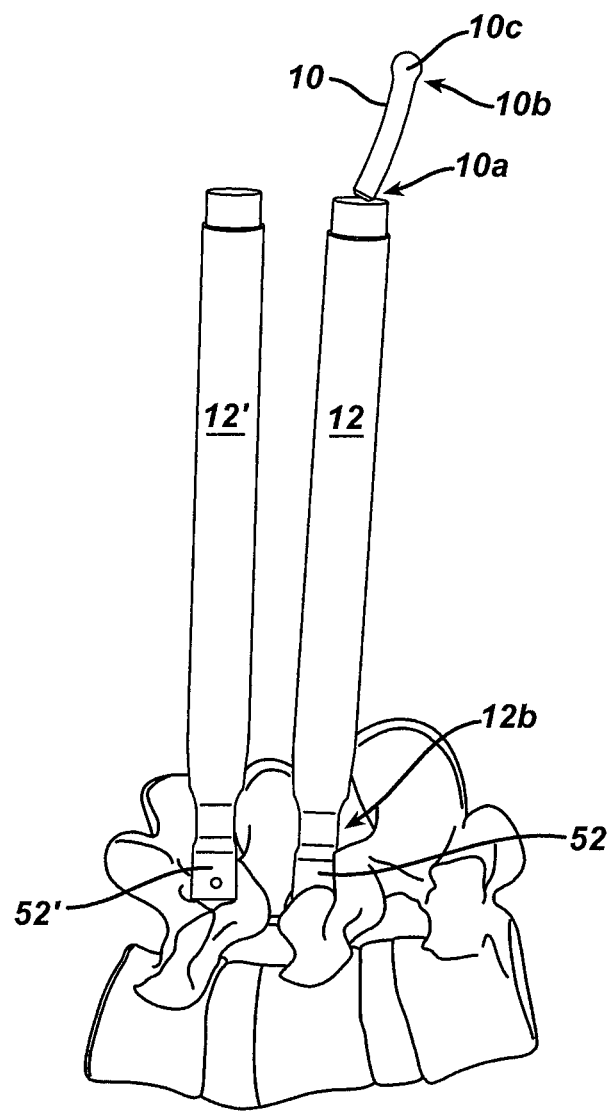
FIG. 6A is a perspective view illustration of first and second access devices coupled to first and second spinal anchors implanted in adjacent vertebrae in a patient's spinal column, showing the spinal fixation element of FIG. 1A being introduced through a proximal end of the first access device with the feature trailing.
Figure 6B:
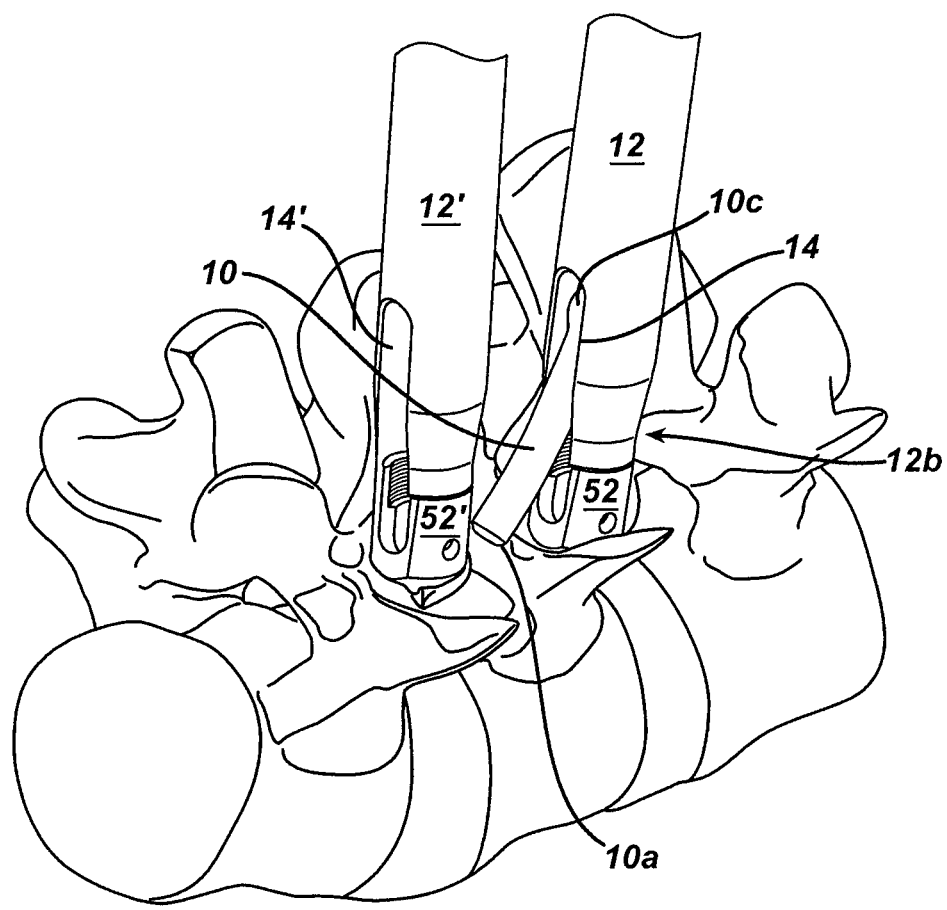
FIG. 6B is a perspective view illustration of the spinal fixation element shown in FIG. 6A being manipulated to extend through the opening of the first access device.
Figure 6C:
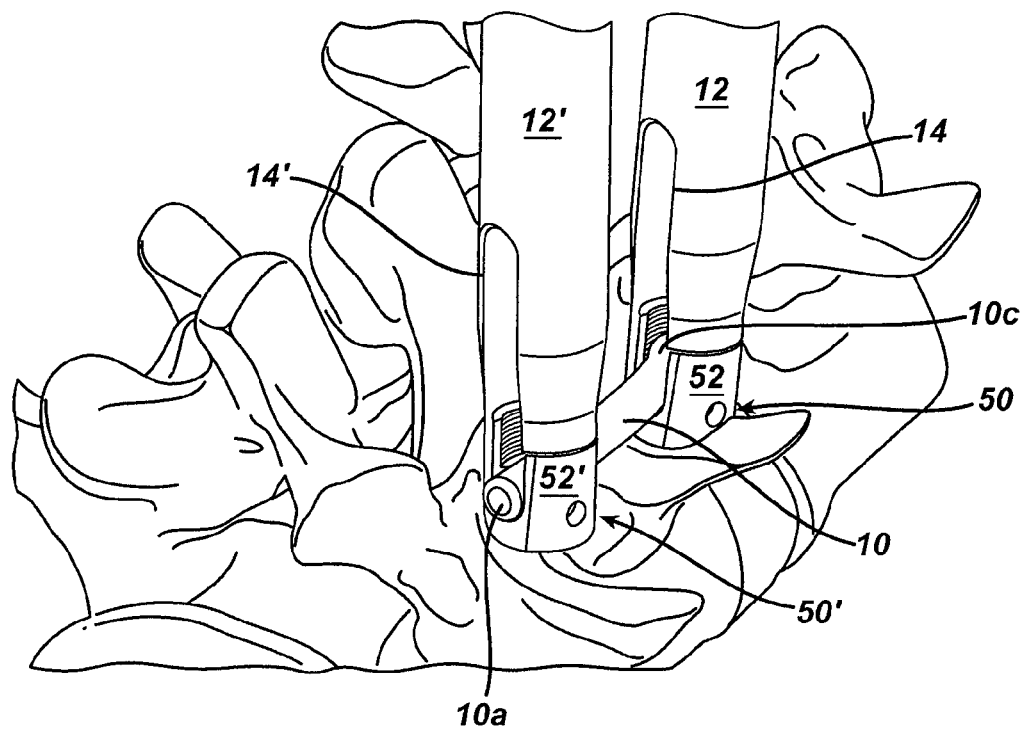
FIG. 6C is a perspective view illustration of the spinal fixation element shown in FIG. 6B being further manipulated to be positioned within the spinal anchor attached to the second access device and disposed within an adjacent vertebra.

FIG. 6A-6D illustrate another embodiment of a method for implanting a spinal fixation element having a feature formed thereon through an access device. In this embodiment, the spinal fixation element 10 is inserted into the access device 12 in a lengthwise orientation with the feature 10c trailing, as shown in FIG. 6A. As the fixation element 10 approaches the distal end 12b of the access device 12, as shown in FIG. 6B, the spinal fixation element 10 can be manipulated to cause the spinal fixation element 10 to transition to the second orientation. This is achieved by passing the leading end 10a of the spinal fixation element 10 through the slot 14 in the access device 12 as the fixation element 10 is moved distally. Further movement of the fixation element 10 will cause the fixation element 10 to be positioned in relation to one or more spinal anchors, and more preferably to extend between the spinal anchor 52 coupled to the access device 12 and a spinal anchor 52' implanted in an adjacent vertebra, as shown in FIG. 6C. As previously stated, a variety of pusher devices can be used to guide and/or manipulate the spinal fixation element 10 to extend through the slot 14. During transition of the spinal fixation element 10, the feature 10c on the fixation element 10 will be captured by the access device 12 and thus it will be seated within the receiver head 52 of the spinal anchor 50 that is coupled to the access device 12, as is also shown in FIG. 6C. A locking mechanism can then be applied to the spinal anchor(s) 50, 50' to lock the spinal fixation element 10 thereto. A person skilled in the art will appreciate that, depending on the type of spinal anchor used, the fixation element 10 can be positioned to be directly or indirectly mated to the spinal anchor(s) 50, 50'.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal implant kit, comprising:
an access device having an inner lumen extending between proximal and distal ends, and at least two sidewall openings formed in a sidewall thereof, the at least two sidewall openings extending from the distal end of the access device and terminating distal to the proximal end of the access device; and
a spinal fixation element having a feature formed thereon adjacent to a terminal end thereof, the feature being sized to allow the feature to be passed through proximal and distal end openings and to be positioned within the inner lumen, and the feature being sized to prevent passage of the feature through either of the at least two sidewall openings in the access device along an entire longitudinal length of each of the at least two sidewall openings.

2. The spinal implant kit of claim 1, wherein the feature comprises a bulbous protrusion formed on the terminal end of the spinal fixation element.

3. The spinal implant kit of claim 2, wherein the bulbous protrusion includes a substantially flattened portion.

4. The spinal implant kit of claim 1, wherein the feature comprises a protrusion extending radially outward from the spinal fixation element.

5. The spinal implant kit of claim 1, wherein the at least two sidewall openings each have a length that is greater than a length of the spinal fixation element.

6. The spinal implant kit of claim 1, wherein the at least two sidewall openings are opposed to one another.

7. The spinal implant kit of claim 1, further comprising a pusher member adapted to advance the spinal fixation element in a distal direction within the access device.

8. The spinal implant kit of claim 7, wherein the pusher member comprises an elongate shaft having a proximal handle portion and a distal portion that is slidably disposable within and extends into at least one of the at least two sidewall openings formed in the sidewall of the access device.

9. The spinal implant kit of claim 1, further comprising a pusher member that is slidably disposable within at least one of the at least two sidewall openings formed in the sidewall of the access device such that it is effective to cause a portion of the spinal fixation element to extend through the at least one of the at least two sidewall openings formed in the sidewall.

10. The spinal implant kit of claim 9, further comprising an actuating member adapted to move the pusher member between a first proximal position and a second distal position.

11. A spinal implant kit, comprising:
an access device having an inner lumen extending between proximal and distal ends, and at least one opening formed in a sidewall thereof adjacent to the distal end; and
a spinal fixation element having only one bulbous protrusion formed thereon adjacent to a terminal end thereof, the spinal fixation element having a longitudinal length less than a longitudinal length of the at least one opening, and the bulbous protrusion having a maximum diameter greater than a maximum width of the at least one opening such that the bulbous protrusion cannot pass through the at least one opening.

12. The spinal implant kit of claim 11, wherein the maximum diameter of the bulbous protrusion prevents passage of the bulbous protrusion through the at least one opening along the longitudinal length of the at least one opening.

13. The spinal implant kit of claim 11, wherein the at least one opening comprises first and second opposed openings formed in the sidewall of the access device, the length of the spinal fixation element being less than lengths of each of the first and second opposed openings, and the maximum diameter of the bulbous protrusion being greater than maximum widths of the each of the first and second opposed openings such that the bulbous protrusion cannot pass through either of the first and second opposed openings.

14. The spinal implant kit of claim 11, wherein the at least one opening in the access device extends from the distal end of the access device and terminates distal to the proximal end of the access device.

15. A spinal implant kit, comprising:
a bone screw having a spinal rod receiving end;
an elongate tubular access device having an inner lumen extending between proximal and distal ends, and first and second openings formed in opposed sidewalls thereof adjacent to the distal end, the elongate tubular access device being configured to mate to the rod receiving end; and
a spinal rod having only one feature formed thereon adjacent to a terminal end thereof, the feature being sized to prevent passage of the feature through any portion of each of the first and second openings in the access device.

16. The spinal implant kit of claim 15, wherein each of the first and second openings has a maximum width that is less than a maximum width of the feature.

17. The spinal implant kit of claim 15, wherein the first and second openings each extend from a terminal distal end of the access device and terminate distal to the proximal end of the access device.